US012708755B2

(12) United States Patent
Grauwinkel et al.

(10) Patent No.: US 12,708,755 B2
(45) Date of Patent: Aug. 18, 2026

(54) BLOOD PUMP

(71) Applicant: Abiomed Europe GmbH, Aachen (DE)

(72) Inventors: Marius Grauwinkel, Aachen (DE); Wolfgang Kerkhoffs, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 600 days.

(21) Appl. No.: 17/437,658

(22) PCT Filed: Mar. 16, 2020

(86) PCT No.: PCT/EP2020/057160
§ 371 (c)(1),
(2) Date: Sep. 9, 2021

(87) PCT Pub. No.: WO2020/187862
PCT Pub. Date: Sep. 24, 2020

(65) Prior Publication Data

US 2022/0161015 A1 May 26, 2022

(30) Foreign Application Priority Data

Mar. 19, 2019 (EP) .................................... 19163665

(51) Int. Cl.
*A61M 60/122* (2021.01)
*A61M 60/13* (2021.01)
(Continued)

(52) U.S. Cl.
CPC .......... *A61M 60/13* (2021.01); *A61M 60/139* (2021.01); *A61M 60/216* (2021.01);
(Continued)

(58) Field of Classification Search
CPC .. A61M 60/122; A61M 60/13; A61M 60/237; A61M 60/422
See application file for complete search history.

(56) References Cited

U.S. PATENT DOCUMENTS 5,964,694 A 10/1999 Siess et al.
2004/0046466 A1 3/2004 Seiss et al.
(Continued)

FOREIGN PATENT DOCUMENTS

CN 102057557 A 5/2011
CN 107302294 A 10/2017
(Continued)

OTHER PUBLICATIONS

Extended European Search Report for European Application No. 19163665.3 dated Sep. 19, 2019 (6 pages).
(Continued)

*Primary Examiner* — Michael J D'Abreu
(74) *Attorney, Agent, or Firm* — BOTOS CHURCHILL IP LAW LLP

(57) ABSTRACT

This invention concerns an intravascular blood pump for percutaneous insertion into a patient's blood vessel. The blood pump comprises a pump casing having a blood flow inlet and a blood flow outlet, an impeller arranged in said pump casing so as to be rotatable about an axis of rotation. The impeller has blades sized and shaped for conveying blood from the blood flow inlet to the blood flow outlet. The blood pump comprises a drive unit for rotating the impeller, the drive unit comprising a plurality of posts arranged about the axis of rotation and a back plate connecting rear ends of the parts, the posts and the back plate together forming a magnetic core of the drive unit. A coil winding is disposed around each of the posts. The coil windings are controllable so as to create a rotating magnetic field, wherein the impeller comprises a magnetic structure arranged to interact with the rotating magnetic field so as to cause rotation of the impeller. The magnetic core or a part of it comprises a discontinuous soft magnetic material which is discontinuous regarding electric conductivity in a cross-section, wherein at least one
(Continued)

weld is provided at a surface of the discontinuous soft magnetic material. The weld bridges at least one discontinuity regarding electric conductivity in the discontinuous soft magnetic material. Further, the invention concerns a method of manufacturing the magnetic core.

11 Claims, 12 Drawing Sheets

(51) Int. Cl.

| | |
|---|---|
| ***A61M 60/139*** | (2021.01) |
| ***A61M 60/216*** | (2021.01) |
| ***A61M 60/237*** | (2021.01) |
| ***A61M 60/422*** | (2021.01) |
| ***A61M 60/508*** | (2021.01) |
| ***A61M 60/804*** | (2021.01) |

(52) U.S. Cl.
CPC ........ *A61M 60/237* (2021.01); *A61M 60/422* (2021.01); *A61M 60/508* (2021.01); *A61M 60/804* (2021.01)

(56) References Cited

U.S. PATENT DOCUMENTS

| | | | |
|---|---|---|---|
| 2004/0046632 | A1 | 3/2004 | Kumano et al. |
| 2011/0084569 | A1 | 4/2011 | Asano et al. |
| 2011/0238172 | A1 | 9/2011 | Akdis |
| 2011/0316381 | A1 | 12/2011 | Asano et al. |
| 2013/0164161 | A1 | 6/2013 | Schoeb |
| 2014/0030122 | A1 | 1/2014 | Ozaki et al. |
| 2017/0302145 | A1 | 10/2017 | Holenstein et al. |

FOREIGN PATENT DOCUMENTS

| | | | |
|---|---|---|---|
| CN | 108883216 | A | 11/2018 |
| DE | 102006042360 | B3 | 5/2008 |
| EP | 0904630 | B1 | 7/2008 |
| EP | 3222301 | A1 | 9/2017 |
| EP | 3456367 | A1 | 3/2019 |
| GB | 2506932 | A | 4/2014 |
| JP | H11341717 | A | 12/1999 |
| JP | 2001008422 | A | 1/2001 |
| JP | 2008172922 | A | 7/2008 |
| JP | 2010017072 | A | 1/2010 |
| JP | 2012125032 | A | 6/2012 |
| JP | 2017169296 | A | 9/2017 |
| JP | 2017192295 | A | 10/2017 |
| KR | 20100134729 | A | 12/2010 |
| KR | 20180123708 | A | 11/2018 |
| WO | 0241935 | A1 | 5/2002 |
| WO | 2014035354 | A1 | 3/2014 |

OTHER PUBLICATIONS

International Search Report and Written Opinion for International Application No. PCT/EP2020/057160 dated May 20, 2020 (12 pages).
Office Action from corresponding Chinese Patent Application No. 202080022900.X dated Jul. 30, 2023 (23 pp.).
Office Action from corresponding Indian Application No. 202117041985 dated Apr. 18, 2023 (6 pp.).
Written Opinion issued in corresponding Singapore Patent Application No. 11202109012R dated May 30, 2023 (6 pp.).
Office Action from corresponding Chinese Patent Application No. 202080022900.X dated Apr. 27, 2024 (24 pp.).
Office Action from corresponding Japanese Patent Application No. 2021-556705 dated Mar. 5, 2024 (9 pp.).
Office Action issued in corresponding Korean Patent Application No. 102021703364, dated Apr. 23, 2025, (11 pp.).
Office Action in corresponding Japanese Patent Application No. 2021-556705, dated Nov. 26, 2024. 9 Pages (With English Translation).

1
2
3
4
6
10
11
12
13
14
21
22
22
23
24
25
26
31
31
32
37
40
40
44
44
50
420

DL
400
450
511
45
10
51
511
52
45
450
85
50
85
51
85
85
44
511
4
DL
LA
44
424
40
7
LA
424
420
15
32
11
37
31
31
3
12

8
81
W
R 8
81
85
W
DL
DL

81
W
R 81
85
W 812
81
W
811
84

DL
81
811
82
84
83
R

811
B
DL
841
81
842
82
84
83

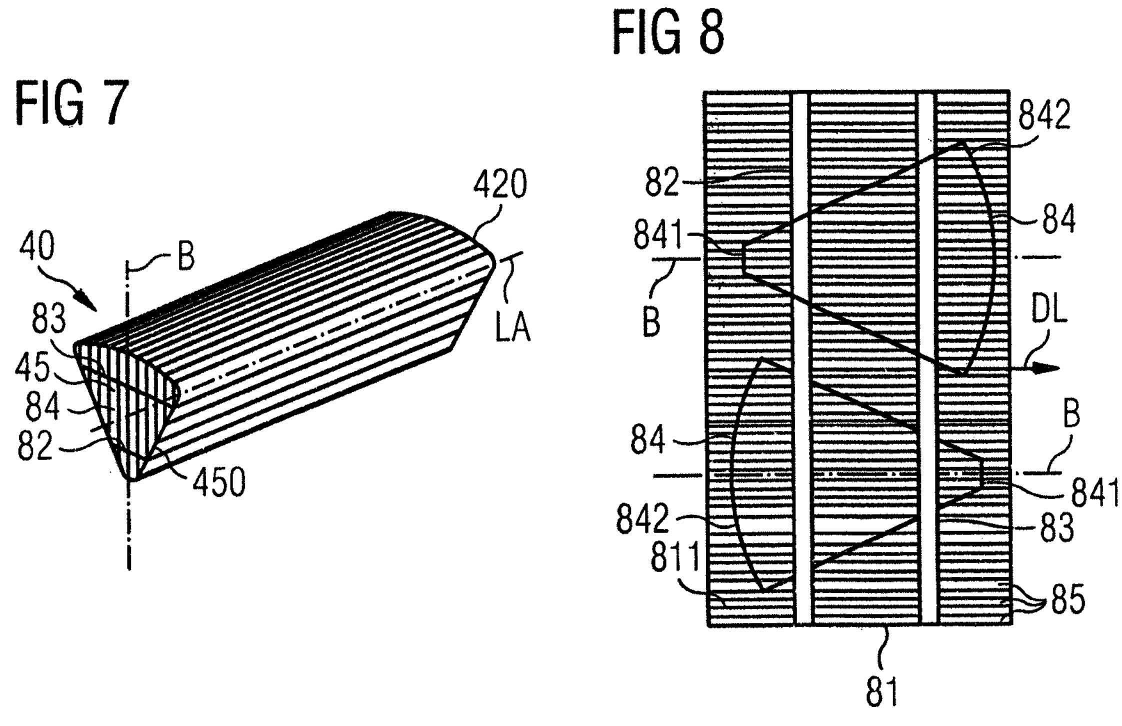
FIG 7
FIG 8
40
B
420
LA
83
45
84
82
450
842
82
841
B
84
DL
B
84
841
842
83
811
85
81
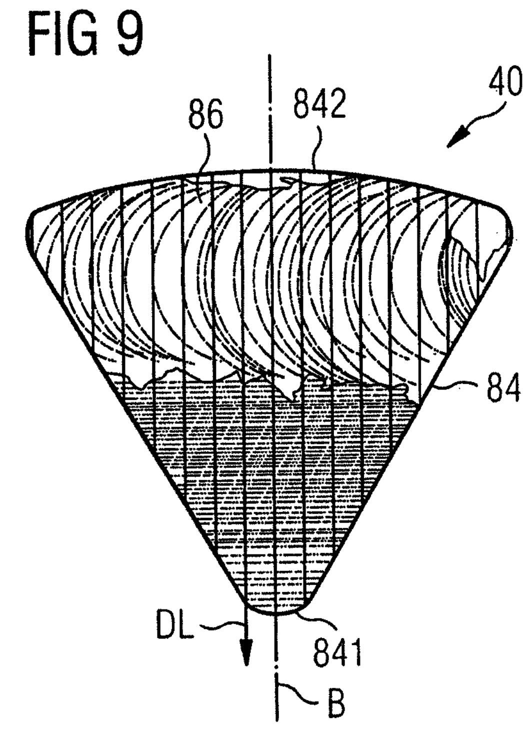
FIG 9
40
86
842
84
DL
841
B 400
450
10
DL
450
85
50
401
401
40
40
4
44
44
420
420
15
32
11
37
31
31
3
12

FIG 12A
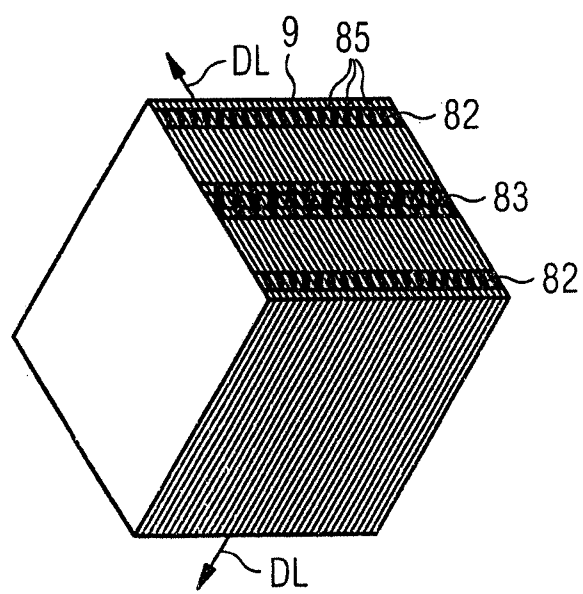
FIG 12B
94
82
DL
400
83
404
401
82
405
85
DL
FIG 12C
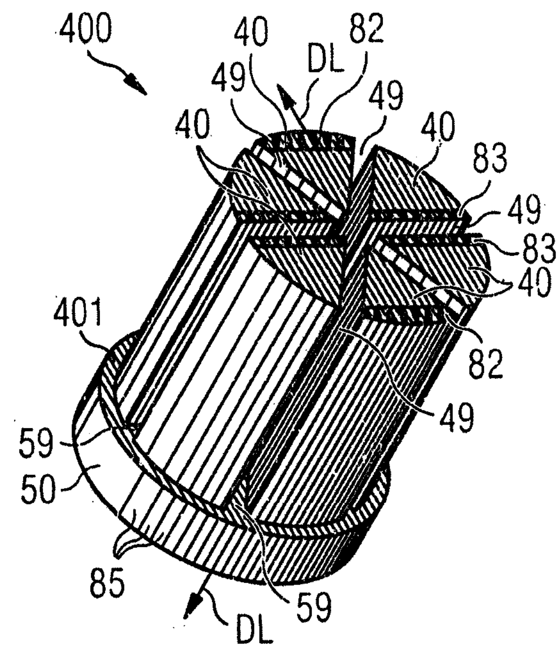

BLOOD PUMP

CROSS-REFERENCE TO RELATED APPLICATIONS

The present application is a national phase entry under 35 U.S.C. § 371 of International Application No. PCT/EP2020/057160, filed Mar. 16, 2020, published as International Publication No. WO 2020/187862 A1, which claims the benefit of the filing date of European Patent Application No. 19163665.3 filed Mar. 19, 2019, the disclosures of which are hereby incorporated herein by reference.

This invention relates to a blood pump, in particular an intravascular blood pump for percutaneous insertion into a patient's blood vessel, to support a blood flow in a patient's blood vessel. The blood pump has an improved drive unit.

BACKGROUND OF INVENTION

Blood pumps of different types are known, such as axial blood pumps, centrifugal (i.e. radial) blood pumps or mixed-type blood pumps, where the blood flow is caused by both axial and radial forces. Intravascular blood pumps are inserted into a patient's vessel such as the aorta by means of a catheter. A blood pump typically comprises a pump casing having a blood flow inlet and a blood flow outlet connected by a passage. In order to cause a blood flow along the passage from the blood flow inlet to the blood flow outlet, an impeller or rotor is rotatably supported within the pump casing, with the impeller being provided with blades for conveying blood.

Blood pumps are typically driven by a drive unit, which can be an electric motor. For instance, US 2011/0238172 A1 discloses extracorporeal blood pumps having an impeller which may be magnetically coupled to an electric motor. The impeller comprises magnets which are disposed adjacent to magnets in the electric motor. Due to attracting forces between the magnets in the impeller and in the motor, rotation of the motor is transmitted to the impeller. In order to reduce the number of rotating parts, it is also known from US 2011/0238172 A1 to utilize a rotating magnetic field, with the drive unit having a plurality of static posts arranged about the axis of rotation, and each post carrying a wire coil winding and acting as a magnetic core. A control unit sequentially supplies a voltage to the coil windings to create the rotating magnetic field. In order to provide a sufficiently strong magnetic coupling, the magnetic forces have to be high enough, which can be achieved by a sufficiently high current supplied to the drive unit or by providing large magnets, which, however, leads to a large overall diameter of the blood pump.

EP 3222301 B1 discloses a blood pump, in particular an intravascular blood pump, having a magnetic coupling between the drive unit and the impeller, wherein the blood pump has a compact design, and in particular a high ratio of pumping power to size of the pump, resulting in sufficiently small outer dimensions to allow the blood pump to be inserted transvascularly, transvenously, transarterially or transvalvularly or being even smaller for reasons of handling and convenience.

More specifically, the blood pump in EP 3222301 B1 comprises a pump casing with a blood flow inlet and a blood flow outlet, an impeller and a drive unit for rotating the impeller. By rotation of the impeller about an axis of rotation and inside of the pump casing, blood can be conveyed from the blood flow inlet to the blood flow outlet by blades of the impeller. The drive unit comprises a plurality of preferably six posts and a back plate connecting rear ends of the posts to act as a yoke. The posts and the back plate make up a magnetic core of the drive unit. The posts are arranged in a circle around the axis of rotation, as seen in a plane which is perpendicular to the axis of rotation, wherein each of the posts has a longitudinal axis, which is preferably parallel to said axis of rotation. The posts each have a coil winding disposed around each of the posts. In order to generate a rotating magnetic field for driving the impeller, the coil windings can be controlled in a coherent manner. The impeller comprises a magnetic structure in the form of a magnet which is arranged to interact with the rotating magnetic field such that the impeller follows its rotation.

It is suggested in unpublished European patent application no. 17191940.0 to keep losses by eddy currents low, a discontinuous soft magnetic material may be used for the magnetically active parts of the drive unit, especially for the posts. A discontinuous material may be for instance a laminated material comprising soft magnetic sheets. However magnetic active parts of the drive unit made of such material tend to disintegrate and fall apart at the layers between the sheets. Another problem occurs in regard of the possibility to manufacture such parts by electric discharge machining. When contacting such a work piece for electric discharge machining at a certain location, not all other locations of the material are in electrical contact with the contacted location. This can complicate electrical discharge machining.

It is an objective of the present invention to facilitate the manufacture of the drive unit for the intravascular blood pump.

SUMMARY OF THE INVENTION

The blood pump of the present invention corresponds to the afore-mentioned blood pump as described in EP 3222 301 B1. Accordingly, it may be an axial blood pump or a diagonal blood pump, which pumps partly axially and partly radially, (the diameter of pure centrifugal blood pumps is usually too large for intravascular applications). However, according to one aspect of the invention, the magnetic core or a part of it, particularly at least one of the posts, comprises or consists of a discontinuous soft magnetic material which is discontinuous regarding electric conductivity in a cross-section transverse to the longitudinal axis of the respective post. At least one weld is provided at a surface of the discontinuous soft magnetic material, especially on at least one post. The weld bridges a discontinuity regarding electric conductivity in the discontinuous soft magnetic material.

Each of the posts has a longitudinal axis. Preferably, the longitudinal axis of each post is parallel to the axis of rotation. The posts each comprise a soft magnetic material which is discontinuous in cross-section transverse, preferably perpendicular, to the longitudinal axis of the respective post. In other words, the soft magnetic material of the posts is discontinuous in cross-section transverse, preferably perpendicular, to a direction of magnetic flux caused by the respective coil winding in the post. By dividing or interrupting the soft magnetic material in cross section, eddy currents in the posts can be reduced or avoided, such that heat generation and energy consumption can be reduced. Reducing energy consumption is particularly useful for long term applications of the blood pump, in which it is desirable that the blood pump is battery-powered to provide mobility for the patient. Also in long term applications, the blood pump may be operated without purge, which is only possible if heat generation is low.

"Discontinuous" in the sense of the present document means that the soft magnetic material as seen in any cross-section transverse to the longitudinal axis is interrupted, separated, intersected or the like by means of insulating material or other materials or gaps in order to form strictly separated areas of soft magnetic material or areas that are interrupted but connected at a different location.

Providing a discontinuous soft magnetic material in cross-sectional planes transverse to the direction of the magnetic flux reduces eddy currents and thus heat generation and energy consumption as explained above. In order not to substantially weaken the magnetic field compared to a continuous or full body (i.e. solid) soft magnetic material, the total amount of soft magnetic material is to be maximized while minimizing the continuous areas of soft magnetic material. This can be achieved for example by providing the soft magnetic material in the form of a plurality of sheets of soft magnetic material, such as electric steel. In particular, the sheets may form a stack of sheets. The sheets are preferably electrically insulated from each other, e.g. by providing adhesive, lacquer, baking enamel or the like between adjacent ones of the sheets. Such arrangement can be denoted as "slotted". Compared to a full body soft magnetic material, the amount of soft magnetic material is recued only little and the amount of insulating material is kept small, such that the magnetic field caused by a slotted post is substantially the same as the magnetic field caused by a solid post. In other words, while heat generation and energy consumption can be reduced significantly, the loss in magnetic field caused by the insulating material is insignificant.

The sheets preferably extend substantially parallel to the longitudinal axis of the respective post. In other words, the sheets may extend substantially parallel to the direction of the magnetic flux, such that the posts are discontinuous in cross-section transverse or perpendicular to the direction of the magnetic flux. It will be appreciated that the sheets may extend at an angle relative to the longitudinal axis of the respective post as long as the soft magnetic material is discontinuous in cross-section transverse to the longitudinal axis. The sheets preferably have a thickness in the range of 25 μm to 1 mm, more preferably 50 μm to 450 μm, for instance 200 μm.

It is generally known to provide slotted soft magnetic material, such as electrical steel, in electric motors to avoid or reduce eddy currents. However, this technology has been applied for large devices in which the sheets usually have a thickness in the range of about 500 μm or higher. In small applications, such as the blood pump of the present invention, in which one of the posts usually has a diameter in said order of magnitude, and in which the power input is relatively low (e.g. up to 20 watts (W)), eddy currents and the associated problems were not expected. Surprisingly, despite the small diameter of the posts, eddy currents and thus heat generation and energy consumption can be reduced by providing slotted posts. This is advantageous for operation of the blood pump, which may be operated at a high speed of up to 50,000 rpm (revolutions per minute).

It will be appreciated that other arrangements than the aforementioned slotted arrangement to provide a discontinuous soft magnetic material in the posts may be possible. For instance, instead of a plurality of sheets, a plurality of wires, fibers, posts or other elongate elements can be provided to form each of the posts of the drive unit. The wires or the like may be provided in the form of a bundle with the wires being electrically insulated from each other, e.g. by means of a coating surrounding each wire or an insulating matrix in which the wires are embedded, and may have various cross-sectional shapes, such as circular, round, rectangular, square, polygonal etc. Likewise, particles of a soft magnetic material, wire wool or other sponge-like or porous structures of soft magnetic material can be provided, in which the space between the areas of soft magnetic material comprises an electrically insulating material, such as an adhesive, lacquer, polymer matrix or the like. A porous and, thus, discontinuous structure of soft magnetic material may also be formed by a sintered material or pressed material. In such structure, an additional insulating material may be omitted because insulating layers may be formed automatically by oxide layers resulting from oxidation of the soft magnetic material by exposure to air.

While the sheets or other structures of soft magnetic material may be formed uniformly, i.e. the sheets within one of the posts or all posts may have the same thickness or wires may have the same diameter, a non-uniform arrangement can be provided. For instance, the sheets may have a varying thickness or the wires may have a varying diameter. More specifically, in particular with regards to a stack of sheets, one or more central sheets may have a larger thickness, while adjacent sheets towards the ends of the stack may have a smaller thickness, i.e. the thickness of the sheets decreases from the center towards the ends of the stack, i.e. towards the outermost sheets of the stack. Similarly, one or more central wires in a bundle of wires may have a larger diameter, while wires at the edge of the post may have a smaller diameter, i.e. the diameter of the wires may decrease from the center towards the edges of the bundle, i.e. towards the outermost wires of the bundle. Providing a larger continuous area of soft magnetic material in the center of the post with respect to a cross-section transverse to its longitudinal axis, i.e. relatively thick sheets or wires in the center, may be advantageous because this may enhance the magnetic flux through the center along the longitudinal axis of each post, and eddy currents in the center are less relevant than eddy currents at the sides of the posts. In other words, such arrangement may be advantageous because eddy currents in the side regions of the posts are more critical and can be reduced by thin sheets or wires in the side regions.

The weld enables the easy manufacture of a magnetic core or a part of it out of a discontinuous soft magnetic material. That is, when separating the magnetic core or the posts for the magnetic core out of a larger work piece of discontinuous soft magnetic material, the discontinuous soft magnetic material may delaminate or otherwise lose its integrity due to the machining forces which are applied on the work piece during the separating process. This is particularly critical due to the very little dimensions of the magnetic core and especially the posts thereof and may even occur when electric discharge machining, especially electric discharge machining by wire cutting, is used for separating the magnetic core, or the posts therefor, out of the work piece. By means of the welds, which are applied on the work piece prior to the separation step, the mechanical stability of the discontinuous material is improved. In the case that electric discharge machining is used for cutting the magnetic core or posts out of the work piece, also the flow of electric current to the location of cutting is improved. The weld or welds may later form a part of the magnetic core or posts.

In particular, an impeller-side end surface of the posts being oriented transverse to the axis of rotation exposes the discontinuous material. Accordingly, the weld or welds may be arranged on the impeller-side surface of the posts. Alternatively or additionally, a weld or welds may be arranged at the rear end surface of the posts or, if the magnetic core including the back plate acting as a yoke is integral with the work piece as a monoblock, a further weld or further welds may be arranged at the rear end surface of the back plate.

Preferably, the rear end surface of at least one of the posts and preferably all of the posts is arranged substantially perpendicular to the longitudinal axis of the at least one of the posts. The at least one of the posts and preferably all of the posts may further comprise a circumferential/peripheral surface disposed about the longitudinal axis of the post and extending along said longitudinal axis, wherein the rear end surface is provided at the rear longitudinal end of said circumferential surface and the rear end surface faces away from the impeller. Preferably, the rear end surface is substantially perpendicular to the circumferential surface.

Preferably, the whole surface of the magnetic core or of a post thereof may be covered with the weld so as to bridge all soft magnetic components, such as sheets of the discontinuous material that are present at the surface. Most preferably, all components of the discontinuous material are bridged. By bridging as many soft magnetic components of the discontinuous material as possible, optimum manufacturing can be achieved.

Preferably, two welds are arranged at one end of the at least one post spaced apart from each other. These welds are preferably weld seams. Such weld seams are preferably arranged in parallel to each other. In particular, spaced-apart seams can be welded onto a surface of a raw material or work piece from which the posts shall be cut after welding.

Alternatively or in addition, the weld or welds may extend over a side surface of the posts. This alternative may cause less eddy currents as the plane of welding is not transverse to the magnetic flux as compared to welding an end surface of the posts.

More than one of the at least one weld may be arranged on a same surface side of the at least one of the posts, be it a side surface or an end surface or both. Further in the alternative, a weld may at least partially surround a side surface of the post.

Preferably, the weld or welds are provided as weld seams. A seam may have a small cross-section in comparison to a weld which covers the entire surface, such that a seam may cause less additional eddy currents.

Like the posts, the back plate may comprise a discontinuous soft magnetic material. Since the magnetic flux in the back plate is substantially transverse or perpendicular to the axis of rotation, the soft magnetic material of the back plate is preferably discontinuous in cross-section parallel to the axis of rotation. An exception may be the case that the posts and the back plate are manufactured as a monoblock. Apart from that, substantially all features and explanations mentioned above with respect to the discontinuous material of the posts are valid also for the back plate. For instance, like the posts, the back plate may be slotted, i.e. may be formed of a plurality of stacked sheets, and the sheets of the back plate are preferably electrically insulated from each other. The sheets of the back plate may extend substantially perpendicularly to the sheets of the post. As explained in the afore-mentioned, eddy currents and thereby heat generation and power consumption can be reduced. However, the back plate may be alternatively formed of continuous, i.e. solid, soft magnetic material.

The back plate, like the posts, is preferably made of a soft magnetic material, such as electrical steel (magnetic steel) or other material suitable for closing the magnetic flux circuit, preferably cobalt steel. The diameter of the back plate may be in the range of 3 mm to 9 mm, such as 5 mm or 6 mm to 7 mm. The thickness of the back plate may be in the range of 0.5 mm to 2.5 mm, such as 1.5 mm. The outer diameter of the blood pump may be in the range of 4 mm to 10 mm, preferably 7 mm. The outer diameter of the arrangement of the plurality of posts may be in the range of 3 mm to 8 mm, such as 4 mm to 7.5 mm, preferably 6.5 mm.

As stated above, the posts are made of a soft magnetic material such as electrical steel (magnetic steel). The posts and the back plate may be made of the same material. Preferably, the drive unit, including the posts and the back plate, is made of cobalt steel. The use of the cobalt steel contributes to reducing the pump size, in particular the diameter. With the highest magnetic permeability and highest magnetic saturation flux density among all magnetic steels, cobalt steel produces the most magnetic flux for the same amount of material used.

The dimensions of the posts, in particular length and cross-sectional area, may vary and depend on various factors. In contrast to the dimensions of the blood pump, e.g. the outer diameter, which depend on the application of the blood pump, the dimensions of the posts are determined by electromagnetic properties, which are adjusted to achieve a desired performance of the drive unit. One of the factors is the flux density to be achieved through the smallest cross-sectional area of the posts. The smaller the cross-sectional area, the higher is the necessary current to achieve the desired magnetic flux. A higher current, however, generates more heat in the wire of the coil due to electrical resistance. That means, although "thin" posts are preferred to reduce the overall size, this would require high current and, thus, result in undesired heat. The heat generated in the wire also depends on the length and diameter of the wire used for the coil windings. A short wire length and a large wire diameter are preferred in order to minimize the winding loss (referred to as "copper loss" or "copper power loss" if copper wires are used, which is usually the case). In other words, if the wire diameter is small, more heat is generated compared to a thicker wire at the same current, a preferred wire diameter being e.g. 0.05 mm to 0.2 mm, such as 0.1 mm. Further factors influencing the post dimensions and the performance of the drive unit are the number of windings of the coil and the outer diameter of the windings, i.e. the post including the windings. A large number of windings may be arranged in more than one layer around each post, for instance, two or three layers may be provided. However, the higher the number of layers, the more heat will be generated due to the increased length of the wire in the outer layers having a larger winding diameter. The increased length of the wire may generate more heat due to the higher resistance of a long wire compared to a shorter one. Thus, a single layer of windings with a small winding diameter would be preferred. A typical number of windings, which in turn depends on the length of the post, may be about 50 to about 150, e.g. 56 or 132. Independent of the number of windings, the coil windings are made of an electrically conductive material, in particular metal, such as copper or silver. Silver may be preferred to copper because silver has an electrical resistance which is about 5% less than the electrical resistance of copper.

Preferably, the posts have a triangular cross section transverse to the axis of rotation and the soft magnetic sheets of soft magnetic material are preferably oriented in or parallel to a plane through a bisecting line of the triangular cross section. This orientation has the advantage that the longest soft magnetic sheet is arranged in the middle of the post. In a mounted state of the post, the bisecting line may run through a radially innermost corner of the triangular cross section and preferably further through the axis of rotation.

In a further aspect of the invention, a method of manufacturing a magnetic core, or a part of a magnetic core, for a drive unit of an intravascular blood pump is proposed. It comprises the following steps in sequence: providing a work piece comprising or consisting of discontinuous soft magnetic material which is discontinuous regarding electric conductivity in a cross-section of the work piece and from which the magnetic core or a part of it is to be manufactured, providing a weld at a surface of the work piece such that the weld bridges at least one discontinuity regarding electric conductivity in the discontinuous soft magnetic material of the work piece, and separating the magnetic core or the part of the magnetic core out of the work piece after the provision of the weld.

At least a part of the weld may remain at the post after separating the magnetic core or the part of the magnetic core out of the work piece. Then, for example, the sheets of a laminated soft magnetic material may securely be held together by the weld.

According to a preferred embodiment, the step of separating the magnetic core or the part of the magnetic core out of the work piece comprises separating at least one of the posts out of the work piece by electric discharge machining (EDM), especially electric discharge machining by wire-cutting. It is preferred that, before machining the posts out of the work piece of soft magnetic material, one dimension of the work piece is pre-cut to the length of a post such that the pre-cut work piece has an outer dimension identical with the length of a post. At the end surfaces that define the length of the posts, the welds can be provided prior to cutting out the posts. For example, one or preferably two weld seams may be placed spaced apart across each of the surfaces of the pre-cut work piece which will later form the cross-sectional end surfaces of the posts to be cut out of the work piece. Preferably, all soft magnetic components of the discontinuous soft magnetic material of the posts to be cut out are electrically connected by the weld. A weld seam may extend over the cross-sections of more than one post that is to be cut out of the work piece. In particular, the weld seam preferably extends from one edge of the pre-cut work piece to an opposite edge of the pre-cut work piece, wherein it also extends across at least one cross-section of a post to be cut out. More than one post may be machined from one pre-cut work piece. The cross-sections of the posts that are to be cut out may be appropriately distributed in the pre-cut material to utilize a high percentage of the material. As mentioned, the discontinuous soft magnetic material of the work piece may be a laminated material comprising laminations of soft magnetic sheets. For example, the triangular cross-sections of two posts to be cut out from the work piece may be oriented such that a bisecting line of a corner in each of the triangular cross-sections is aligned with a lamination plane of the soft magnetic material, wherein the bisecting lines have a distance to each other and the corners of the triangular cross-sections with the bisecting lines point in opposite directions. The aforementioned measures help to efficiently produce the posts from the work piece.

Preferably, in respect of triangular posts, the weld or welds may be arranged along one triangle side of the triangular cross-section of the posts. Then, the posts may be mechanically stabilized from this side. This way, the laminated sheets of soft magnetic material may be electrically connected by the weld, preferably all sheets of the posts.

Preferably, at least one weld is produced by laser welding. It is also possible to apply two-fold laser welding whereby a location of the weld is welded at least once again. This may be helpful for bridging a gap between two neighboring sheets of a laminated soft magnetic material, for example.

A cut-out magnetic core or a part of the magnetic core, particularly a cut-out post, may be deburred at the at least one weld after separating the magnetic core or the part of the magnetic core out of the work piece. Burrs can possibly penetrate an electrical insulation.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings:

FIG. 7 shows a perspective view of a post which is separated out of the intermediate product as prepared according to FIGS. 5A to 6C;

FIG. 8 shows a front view on a plane of the intermediate product of FIG. 6A with two weld seams and two cross sections of posts that are to be cut out of the intermediate product;

FIG. 9 shows a front view of an end surface of a post with a weld;

FIGS. 12A to 12C show welds on the integrated magnetic core as manufactured according to FIGS. 11A to 11C.

DETAILED DESCRIPTION

Figure 1:
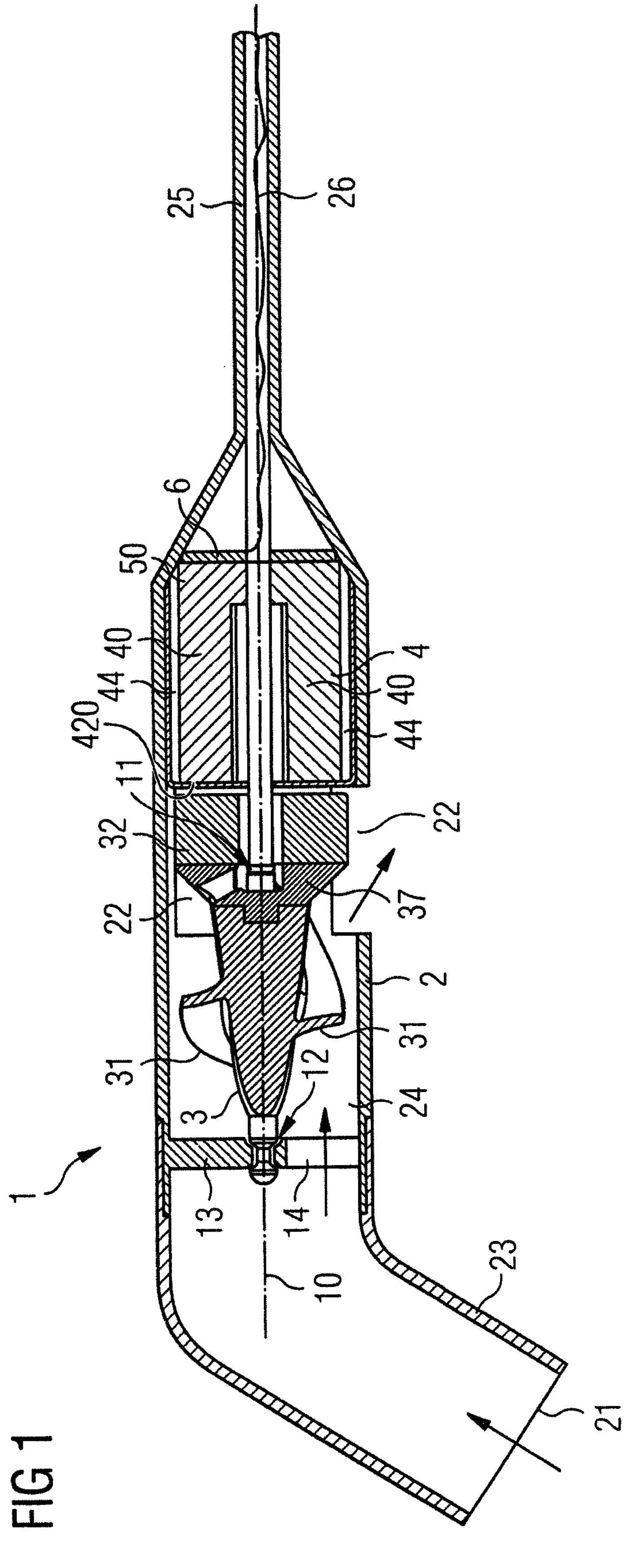
FIG. 1 shows a cross-sectional view of a blood pump.

Referring to FIG. 1, a cross-sectional view of a blood pump 1 is illustrated. The blood pump 1 comprises a pump casing 2 with a blood flow inlet 21 and a blood flow outlet 22. The blood pump 1 is designed as an intravascular pump, also called a catheter pump, and is deployed into a patient's blood vessel by means of a catheter 25. The blood flow inlet 21 is at the end of a flexible cannula 23 which may be placed through a heart valve, such as the aortic valve, during use.

The blood flow outlet 22 is located in a side surface of the pump casing 2 and may be placed in a heart vessel, such as the aorta. The blood pump 1 is electrically connected with an electric line 26 extending through the catheter 25 for supplying the blood pump 1 with electric power in order to drive the pump 1 by means of a drive unit 4, as explained in more detail below.

If the blood pump 1 is intended to be used in long term applications, i.e. in situations in which the blood pump 1 is implanted into the patient for several weeks or even months, electric power is preferably supplied by means of a battery. This allows a patient to be mobile because the patient is not connected to a base station by means of cables. The battery can be carried by the patient and may supply electric energy to the blood pump 1, e.g. wirelessly.

The blood is conveyed along a passage 24 connecting the blood flow inlet 21 and the blood flow outlet 22 (blood flow indicated by arrows). An impeller 3 is provided for conveying blood along the passage 24 and is mounted to be rotatable about an axis of rotation 10 within the pump casing 2 by means of a first bearing 11 and a second bearing 12. The axis of rotation 10 is preferably the longitudinal axis of the impeller 3. Both bearings 11, 12 are contact-type bearings in this embodiment. At least one of the bearings 11, 12 could be a non-contact-type bearing, however, such as a magnetic or hydrodynamic bearing. The first bearing 11 is a pivot bearing having spherical bearing surfaces that allow for rotational movement as well as pivoting movement to some degree. A pin 15 is provided, forming one of the bearing surfaces. The second bearing 12 is disposed in a supporting member 13 to stabilize the rotation of the impeller 3, the supporting member 13 having at least one opening 14 for the blood flow. Blades 31 are provided on the impeller 3 for conveying blood once the impeller 3 rotates. Rotation of the impeller 3 is caused by the drive unit 4 which is magnetically coupled to a magnet 32 at an end portion of the impeller 3. The illustrated blood pump 1 is a mixed-type blood pump, with the major direction of flow being axial. It will be appreciated that the blood pump 1 could also be a purely axial blood pump, depending on the arrangement of the impeller 3, in particular the blades 31.

The blood pump 1 comprises the impeller 3 and the drive unit 4. The drive unit 4 comprises a plurality of posts 40, such as six posts 40, only two of which are visible in the cross-sectional view of FIG. 1. The posts 40 are arranged parallel to the axis of rotation 10, more specifically, a longitudinal axis of each of the posts 40 is parallel to the axis of rotation 10. One end of the posts 42 is disposed adjacent to the impeller. Coil windings 44 are arranged about the posts 40. The coil windings 44 are sequentially controlled by a control to create a rotating magnetic field. A part of the control unit is the printed circuit board 6 which is connected to the electric line 26. The impeller has a magnet 32, which is formed as a multiple piece magnet in this embodiment. The magnet 32 is disposed at the end of the impeller 3 facing the drive unit 4. The magnet 32 is arranged to interact with the rotating magnetic field so as to cause rotation of the impeller 3 about the axis of rotation 10.

In order to close the magnetic flux path, a back plate 50 is located at the end of the posts 40 opposite the impeller-side of the posts. The posts 40 act as a magnetic core and are made of a suitable material, in particular a soft magnetic material, such as steel or a suitable alloy, in particular cobalt steel. Likewise, the back plate 50 is made of a suitable soft magnetic material, such as cobalt steel. The back plate 50 enhances the magnetic flux, which allows for reduction of the overall diameter of the blood pump 1, which is important for intravascular blood pumps. For the same purpose, a yoke 37, i.e. an additional impeller back plate, is provided in the impeller 3 at a side of the magnet 32 facing away from the drive unit 4. The yoke 37 in this embodiment has a conical shape in order to guide the blood flow along the impeller 3. The yoke 37 may be made of cobalt steel, too. One or more wash-out channels that extend towards the central bearing 11 may be formed in the yoke 37 or the magnet 32.

Figure 2:
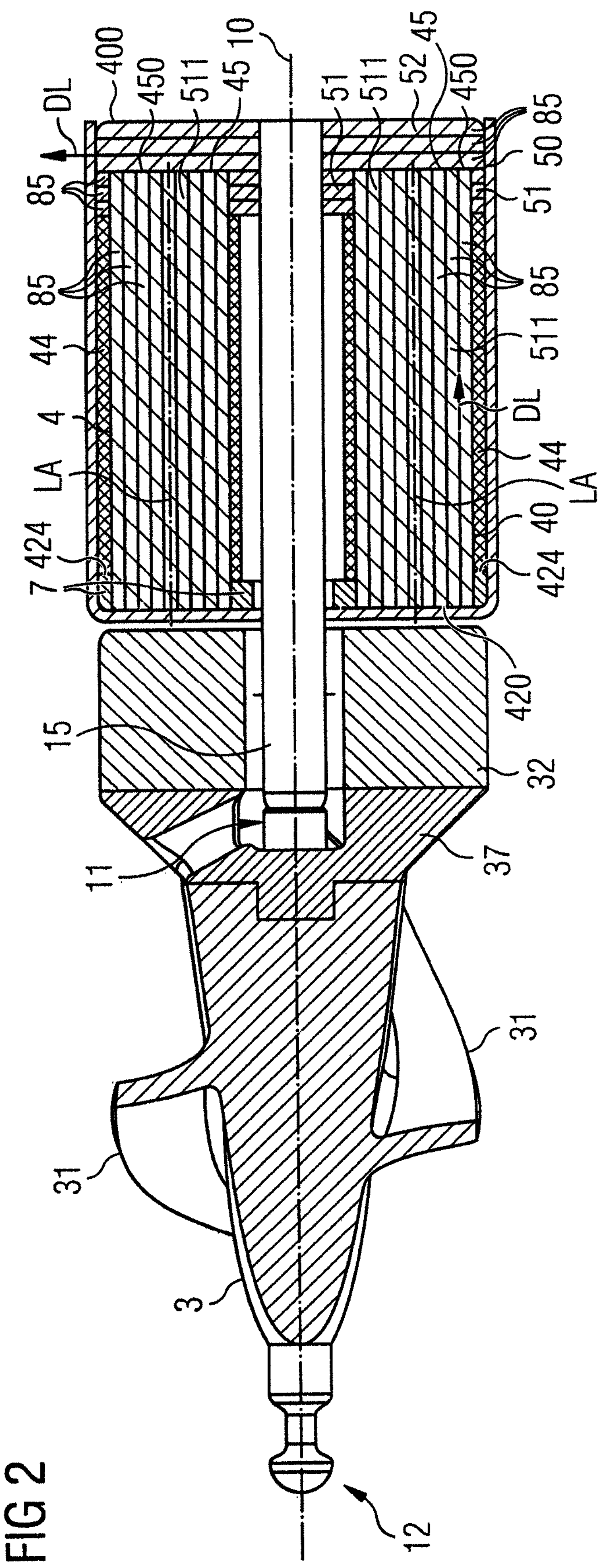
FIG. 2 shows a cross-sectional view of a preferred embodiment of a drive unit-impeller-arrangement.

FIG. 2 shows a cross-sectional view of a preferred embodiment of a drive unit-impeller-arrangement for the blood pump according to FIG. 1. As can be seen in FIG. 2, the impeller-side ends 420 of the posts 40 do not extend radially over the windings 44. Rather, the cross section of the posts 40 is constant in the direction of a longitudinal axis LA of the posts 40. It is thus avoided that the posts 40 come close to each other, as this could cause a partial magnetic short-circuit with the result of a reduced power of the electric motor of the blood pump.

The drive unit according to FIG. 2 may comprise at least two, at least three, at least four, at least five or preferably six posts 40. Higher numbers of posts 40 such as nine or twelve, may be possible. Due to the cross-sectional view, only two posts 40 are visible. The posts 40 and the back plate 50 form a magnetic core 400 of the drive unit 4 which may have a diameter of less than 10 mm.

The posts 40 may, as shown, consist of a discontinuous soft magnetic material that is discontinuous in regard of electric conductivity. The discontinuous soft magnetic material comprises a plurality of sheets 85 which are made of a ferromagnetic material and which are laminated to each other. A direction of lamination is arranged in direction of the longitudinal axis LA of the posts 40 and marked by an arrow DL. As shown, the posts 40 are arranged in parallel to the axis of rotation 10.

A spacer 7 is disposed around the posts 40. It is made of a magnetically inactive material and has the purpose to keep the distance of the posts 40 constant at their impeller-side ends 420. The spacer 7 will be described in further detail in regard of FIGS. 3A to 3C. The impeller-side ends 424 of the coil windings 44 extend up to the spacer 7. At the other ends of the posts 40 is provided the back plate 50. According to the embodiment shown in FIG. 2, the back plate 50 has recesses for receiving therein the posts 40. More specifically, it comprises a first layer 51 with openings 511 for rear ends 450 of the posts 40. The back plate 50 will be described in further detail in regard of FIGS. 4A to 4C.

It is conceivable to realize embodiments of the blood pump 1 with arbitrary combinations of the three above-mentioned features: no radial extension of the impeller-side ends 424 of the posts over the impeller-side ends of the windings 44, provision of a magnetically inactive spacer 7 between the posts 40, and back plate 50 with recesses for receiving the rear ends 450 of the posts 40.

Figure 3A:
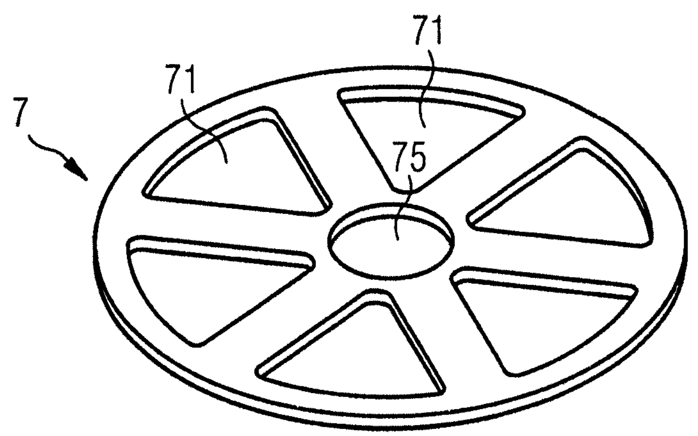
FIG. 3A shows a spacer for the drive unit-impeller-arrangement according to FIG. 2 in a perspective view.
Figure 3B:
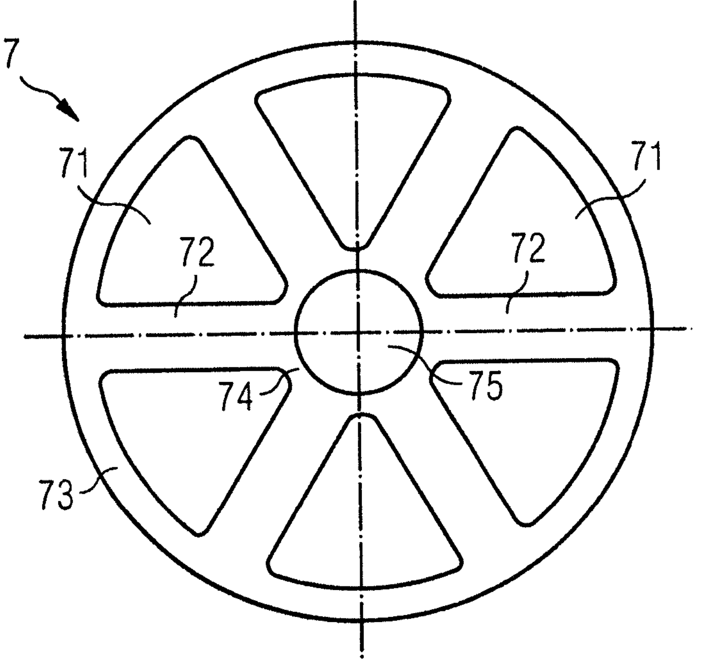
FIG. 3B shows a front view of the spacer of FIG. 3A.
Figure 3C:
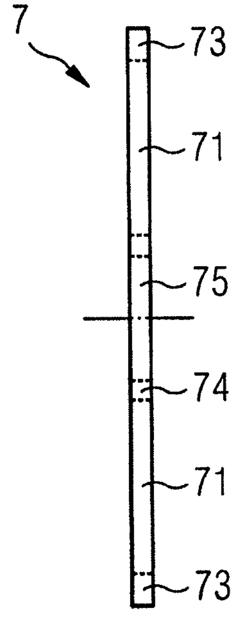
FIG. 3C shows a side view of the spacer of FIGS. 3A and 3B.

FIGS. 3A to 3C show a perspective view, a front view and a side view of the spacer 7, respectively. The spacer 7 generally has the form of a disk or a wheel with a through hole 75 in the middle. The spacer 7 comprises an opening 71 for each of the posts. For an embodiment with six posts 40, six openings 71 are present as shown. Between the openings 71, distancing spokes 72 are arranged. When the posts 40 are inserted in the openings 71, the distancing spokes 72 keep the distance between the posts 40 constant. Further, the spacer 7 comprises an outer rim 73 and an inner rim 74 which connect neighboring distancing spokes 72 and which stabilize the spacer. The spacer 7 is made of titanium which is a paramagnetic material that avoids a magnetic short circuit when arranged between the impeller-side ends 420 of the posts 40. Titanium provides a high mechanical strength such that it allows manufacturing of the spacer 7 with a small thickness. This is advantageous regarding consumption of construction space.

Figure 4A:
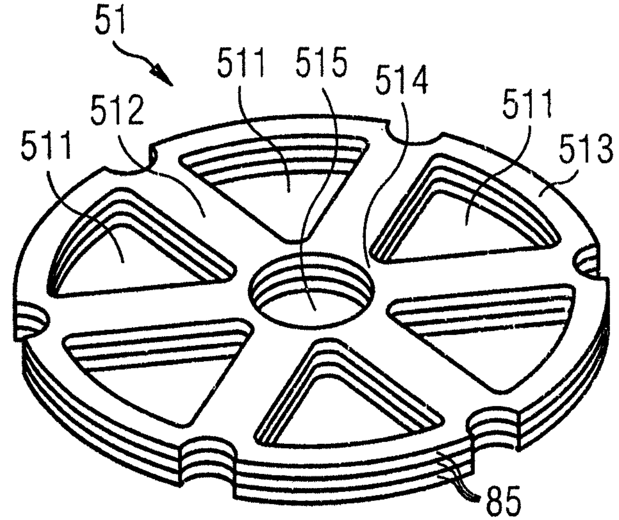
FIG. 4A shows a perspective view of a first layer of a back plate with openings for posts of the drive unit of the arrangement according to FIG. 2.

FIG. 4A shows the perspective view of a first layer 51 of the back plate 50. The first layer 51 has a general shape of a disc or a wheel with a central hole 515. The first layer 52 comprises openings 511 into which the rear ends 450 of the posts 40 will be arranged. The first layer 51 comprises distancing spokes 512 which are arranged between the openings 511. One purpose of the distancing spokes 512 is to keep the distance of the rear ends 450 of the posts 40 constant to each other. Further, the first layer 51 comprises an outer rim 513 and an inner rim 514 which connect the distancing spokes 512 at the outer radial end and the inner radial end of the openings 511, respectively. The first layer 51 may be made of a discontinuous soft magnetic material which is discontinuous in regard of electrical conductivity. It may be made up of several ferromagnetic sheets 85, particularly three sheets, as shown in FIG. 4A. The sheets 85 are laminated together with an electrically non-conductive material to form the discontinuous soft magnetic material. A direction of lamination DL is generally parallel to the sheets 85, and the direction of the main extension of the sheets defines the plane of lamination. Within the back plate 50, the sheets 85 are perpendicular to the axis of rotation 10. In the middle of the first layer 51, a hole 515 is arranged. Its purpose may be to ease the assembly of the first layer 51 and the second layer 52, e.g. centering the first and second layers 51, 52.

Figure 4B:
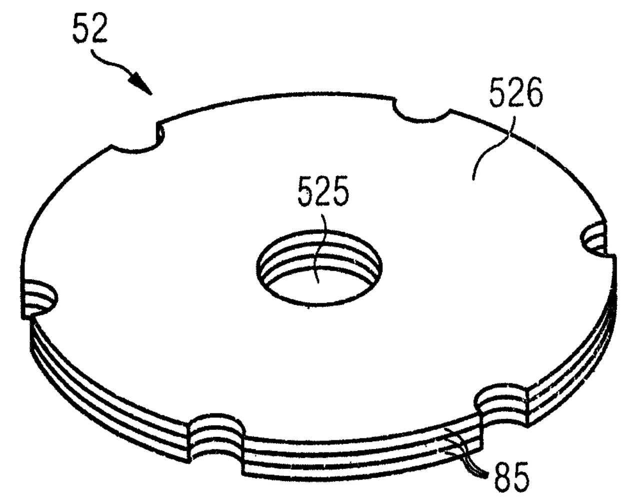
FIG. 4B shows a perspective view of a second layer of the back plate without openings for posts of the drive unit of the arrangement of FIG. 2.

In FIG. 4B, a perspective view of a second layer 52 of the back plate 50 is shown. The second layer 52 substantially has the form of a disk with a hole 525 in the middle corresponding to the hole 515 in the first layer 51. The second layer 52 does not have any openings for the rear ends of the posts 40. Instead, the second layer 52 has a contact plane 526 facing the rear ends 450 of the posts 40. The rear ends 450 of the posts, in an assembled state of the drive unit, are in contact with the contact plane 526 of the second layer 52 of the back plate 50 to transmit magnetic flux between the rear ends 450 of the posts 40 and the back plate 50. As all the rear ends 450 of the posts 40 are in contact with the contact plane 526, magnetic flux can be exchanged between the posts 40, and a magnetic zero point may form in the second layer 52. In order to enable this, the second layer 52 is made of a soft magnetic material. The soft magnetic material may be a discontinuous soft magnetic material which is discontinuous in regard of electric conductivity and may comprise sheets 85 which are laminated together, similar to the structure as described above in relation to the first layer 51. As an example, three sheets 85 as shown in FIG. 4B may make up the second layer 52. In the second layer 52, the direction of lamination D is perpendicular to the axis of rotation 10. The sheets 85 are ferromagnetic and electrically conducting, whereas intermediate layers between the sheets 85, which are not explicitly shown, are non-ferromagnetic and electrically non-conducting. This type of discontinuous soft magnetic material reduces eddy currents which otherwise would be generated to a greater amount by changes of magnetic flux. The hole 525 in the middle of the second layer 52 may have the purpose to ease the assembly of the first layer 51 and the second layer 52, e.g. centering the first and second layers 51, 52.

Figure 4C:
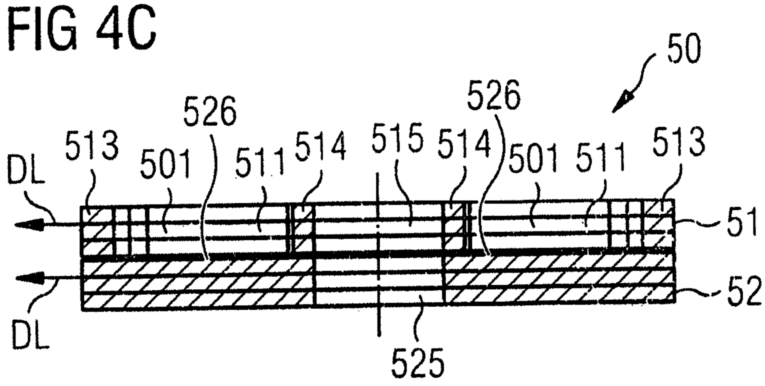
FIG. 4C shows a cross-sectional view of the assembled back plate comprising the first and the second layers of FIGS. 4A and 4B.

FIG. 4C shows a cross-section of the back plate 50. It is composed of the first layer 51 and the second layer 52 which are bonded to each other at their main surfaces having the greatest extension. The bonding between the first layer 51 and the second layer 52 of the back plate 50 can be established in the same manner as between the sheets 85 of the first and the second layers 51, 52. The through holes 515 and 525 of the first layer 51 and the second layer 52 are aligned with each other so as to center the first and second layers 51, 52. By stacking the first and the second layers 51, 52, the openings 511 are closed at one end by the second layer 52 such that recesses 501 are formed for accommodation of the rear ends 450 of the posts 40. At the ground of the recesses 501, the contact plane 526 is formed. When a post 40 is inserted into a recess 501, its rear end 450 gets into contact with the contact plane 526. Furthermore, the position of the post 40 is fixed by the distancing spokes 512 as well as by the outer and the inner rims 513, 514 which together surround each of the posts 40. In this way, a magnetic connection is established between the second layer 52 and the rear end surfaces 45 of posts 40 at the contact plane 526 and, additionally, a second magnetic connection is established between the posts 40 and the above-mentioned surrounding parts of the first layer 51. However, the main part of the magnetic flux is transferred via the contact plane 526. Preferably, the surface at the rear end 450 of the posts 40 has a predefined evenness and the contact plane 526 also has a predefined evenness. This way, gaps between the surface 45 at the rear end 450 of the posts 40 and the contact plane 526 may be kept below a certain size of preferably less than 10 μm. This improves the transfer of magnetic flux between the posts 40 and the back plate 50. Preferably, no additional material is present between the surface 45 at the rear end 450 of the posts 40 and the contact plane 526. In this embodiment of the invention, the transfer of magnetic flux via the surface 45 and the back plate 50 is independent of the manner of fastening the posts 40 to the back plate 50.

Figures 5A, 5B, 5C, 5D:
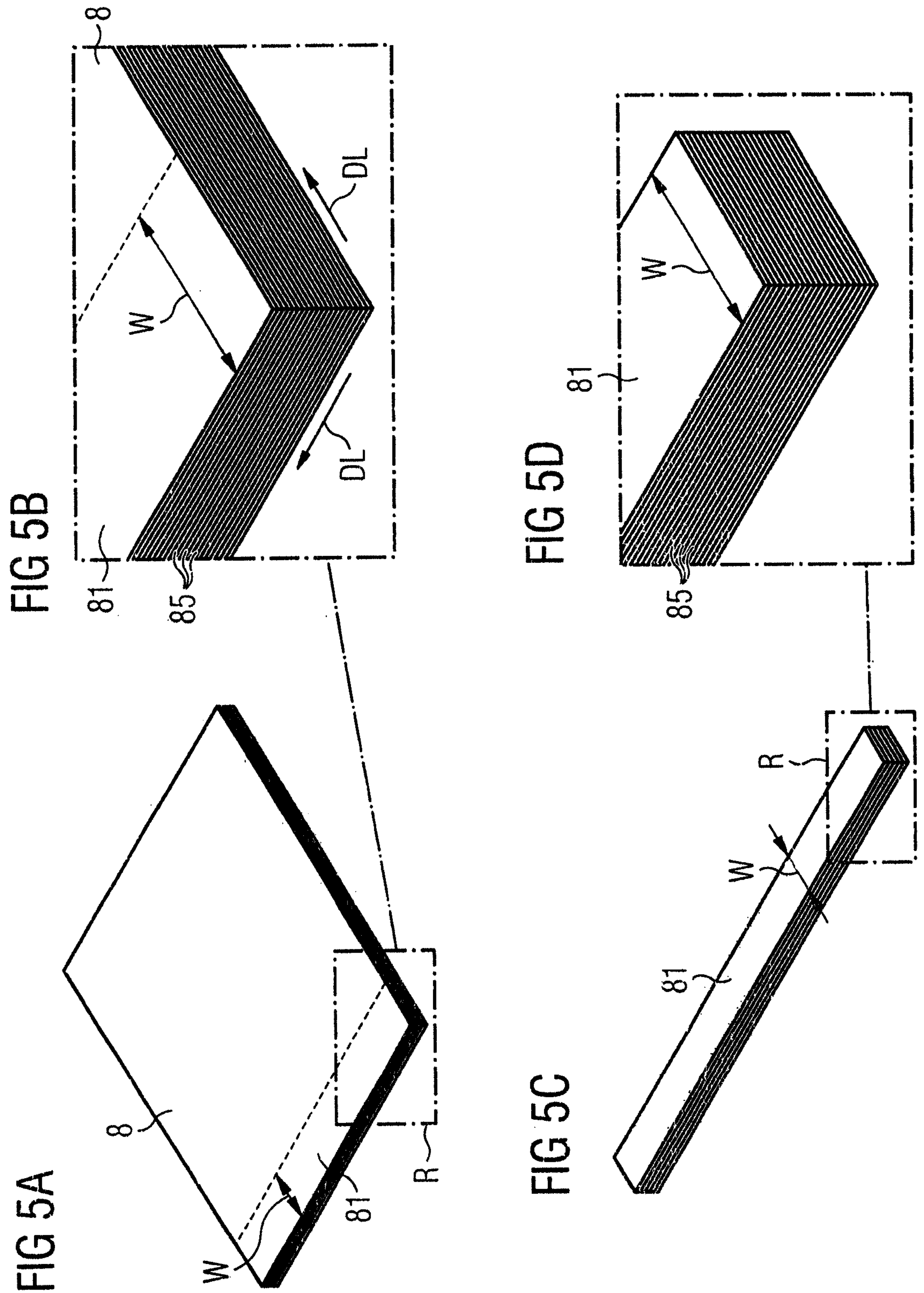
FIGS. 5A to 5D show stages of manufacturing an intermediate product for the further manufacture of posts for the drive unit of the arrangement according to FIG. 2.

FIGS. 5A to 5D show a preparation step for the production of the posts 40. FIG. 5A shows a perspective view of a plate 8 of discontinuous soft magnetic material which is discontinuous regarding electrical conductivity, which is hereinafter also referred as to a work piece.

In FIG. 5A, the plate 8 is marked with a width W for cutting a work piece rod 81 off from the plate 8. The width W of the work piece rod 81 is identical with a length of a post 40 which will be manufactured from the work piece rod 81. An enlarged vieiw of the portion marked by the rectangle R in FIG. 5A is shown in FIG. 5B. Here, stacked sheets 85 of the discontinuous soft magnetic material are visible. The directions of lamination DL runs along the main plane of the plate 8 and, thus, foinis the plane of lamination.

FIG. 5C shows the work piece rod 81 cut-off from the plate 8 as a separate piece of discontinuous material. An enlarged view of the portion marked by the rectangle R in FIG. 5C is shown in FIG. 5D. The sheets 85 of the work piece rod 81 are visible in this enlargement.

Figures 6A, 6B, 6C:
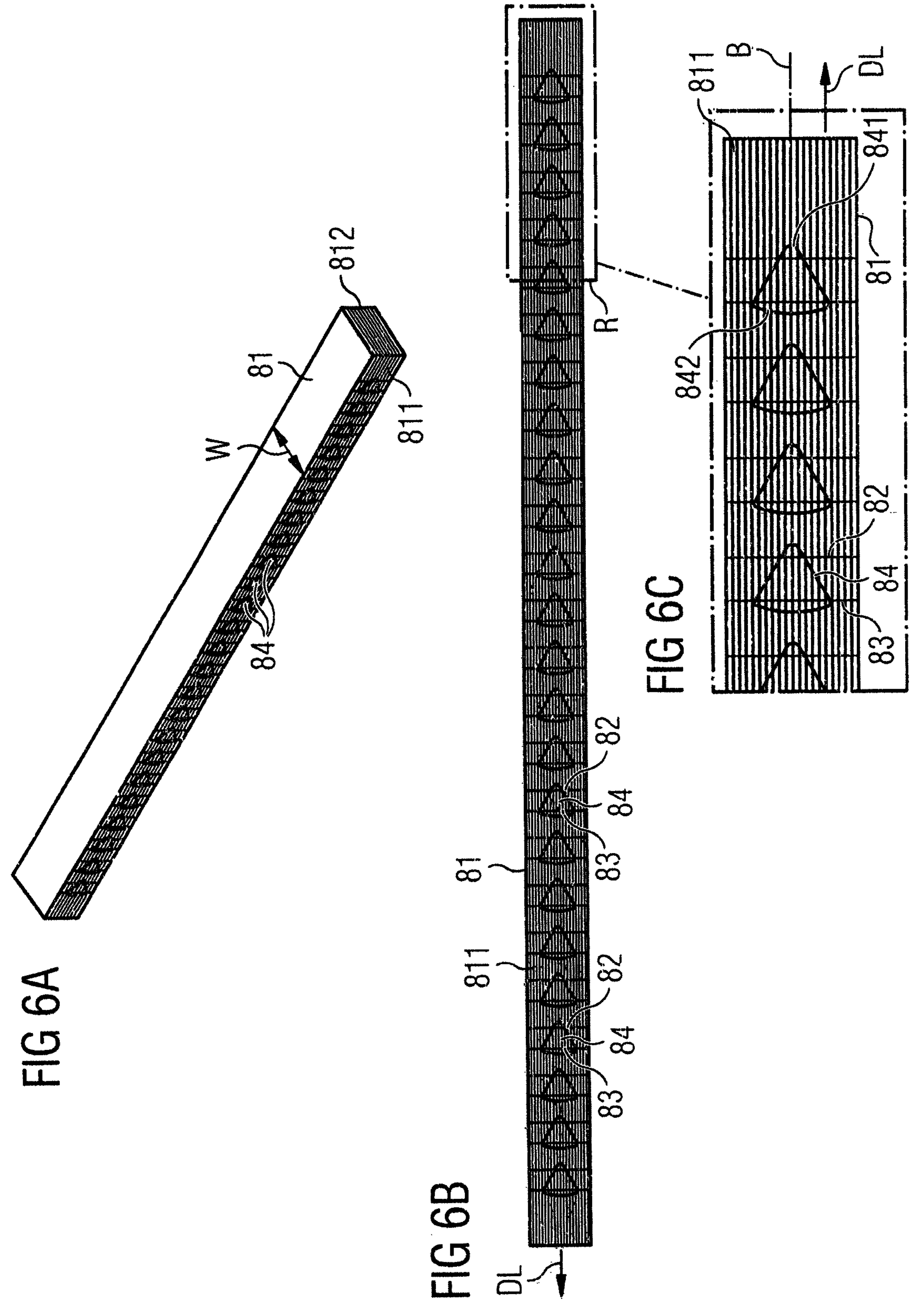
FIGS. 6A to 6C show welds on the intermediate product according to FIG. 5C.

FIG. 6A shows the work piece rod 81 of FIGS. 5C and 5D forming the basis for a welding step in preparation of cutting posts 40 out of the rod 81. On a side plane of the rod 81 pointing to the left side in FIG. 6A, a plurality of cross sections 84 of posts 40 to be manufactured from the rod 81 are depicted. Posts 40 are manufactured by cutting these cross sections 84 out of the rod 81. As the width W of the rod 81 corresponds to the length of the posts 40, the side faces 811 and 812 of the rod 81 become end surfaces at the impeller-side end 420 and the rear end 450 of the posts 40.

FIG. 6B shows of the next preparation step before cutting out the posts 40. Two weld seams 82 and 83 are welded on the face 811 of the rod 81 at a distance to each other and across each of the cross sections 84 of a post 40 to be cut out. The weld seams 82 and 83 run perpendicular to the direction of lamination DL of the sheets 85. In this way, the sheets of the discontinuous material are connected to each other. Instead of two weld seams, a single weld seam may be provided. In addition, similar weld seams may be provided on the opposite side face 812 of the rod 81. The sheets 85 have a better mechanical connection to each other due to the weld seams 82 and 83 and are also electrically connected. The latter has the advantage that electrical current can flow from any position of the discontinuous soft magnetic material which is supposed to become a post 40 to each position of electrical connection of the rod 81 which may be required e.g. for electric discharge machining. This way, electrical discharge machining is facilitated significantly. Furthermore, higher process reliability is achieved as the cut-out posts 40 cannot fall apart by delamination. Preferably, laser welding is applied. It may be advantageous to apply welding power to the same weld twice or even more often. The portion of the rod 81 which is marked by the rectangle R is shown enlarged in FIG. 6C.

Thus, FIG. 6C shows a plurality of cross sections 84 of posts 40 which are to be cut out of the rod 81. The cross sections 84 have a substantially triangular shape. As shown, the corners may be rounded. A convex side 842 of the triangle which is shown at the left side of the cross section 84 in FIG. 6C has a convex form. This type of cross section 84 is advantageous in order to fully utilize the available construction space inside of the cylindrical pump housing 2. A bisector line of a corner 841 of the cross section 84 which is opposite to the convex side 842 of the cross section 84 is aligned with the direction of lamination DL. In this way, the sheets 85 run symmetrically through the cross-section 84.

FIG. 7 shows a post 40 which has been cut out of a rod 81. As can be seen at the surface 45 at the rear end 450 of the rod 81, the weld seams 82 and 83 are still present on this surface. The post 40 has a constant cross section 84 along its entire length. The weld seams 82 and 83 are deburred after cutting out the post 40.

FIG. 8 shows another arrangement of two cross-sections 84 on a side face 811 of a work piece rod 81. In contrast to the work piece rods 81 shown in FIGS. 6A to 6C, the side surface 811 of the work piece rod 81 of FIG. 8 has a size which allows for disposing two cross sections 84 beside each other in a direction perpendicular to the direction of lamination DL. The cross sections 84 are oriented relative to the direction of lamination DL such that the bisector line B of a corner of each of the cross sections 84 opposite to its respective convex side 842 is aligned with the direction of lamination DL. In this way of disposing the cross sections 84 along the rod 81, material can be saved. Less waste material is produced. It is conceivable to stack even more cross sections 84 of posts 40 in a direction perpendicular to the direction of lamination DL, depending on the thickness of the rod 81 and the required cross sectional dimensions of the posts 40. The weld seams 82 and 83 each run across each of the cross sections 84. The weld seams 82, 83 also run across the entire side face 811 of the rod 81 in a direction perpendicular to the direction of lamination DL. In this way, all sheets 85 of the discontinuous soft magnetic material of the rod 81 are connected with each other.

FIG. 9 shows an example of a post 40 cut out from a welded rod 81, namely a front view on one of the end surfaces of the post 40. As shown in FIG. 9, a single weld seam 86 of a considerable width, which may cover more than about one third of the height of the triangular cross section 84, runs along the convex side 842 of the cross-section 84. The weld seam 86 runs perpendicular to the direction of lamination DL to connect all sheets thereof. Again a bisector line B of a corner 841 opposite to the convex side 842 is aligned with the direction of lamination DL.

Figure 10:
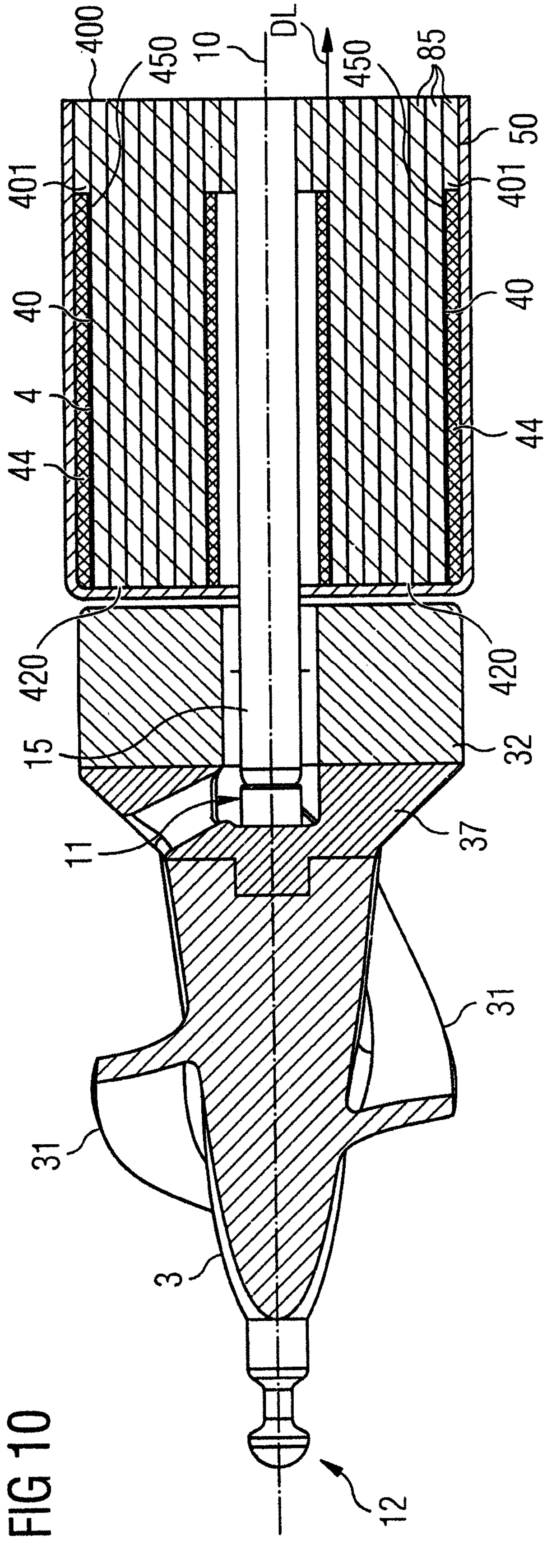
FIG. 10 shows a cross-sectional view of a second embodiment of a drive unit-impeller-arrangement.

FIG. 10 shows a second embodiment of a drive unit-impeller-arrangement for the blood pump 1 according to FIG. 1. Similar to the first embodiment shown in FIG. 2, the impeller-side ends 420 of the posts 40 do not extend radially over the windings 44. Rather, the cross section of the posts 40 is constant in the direction of a longitudinal axis LA of the posts 40. It is thus avoided that the posts 40 come close to each other, as this could cause a partial magnetic short-circuit with the result of a reduced power of the electric motor of the blood pump.

The drive unit according to FIG. 10 may comprise at least two, at least three, at least four, at least five or preferably six posts 40. Higher numbers of posts 40 such as eight, ten or twelve, may be possible. Due to the cross-sectional view, only two posts 40 are visible. The posts 40 and the back plate 50 form a magnetic core 400 of the drive unit 4 which may have a diameter of less than 10 mm.

This embodiment differs from the first embodiment shown in FIG. 2 by a different structure of the magnetic core. Here, the magnetic core 400 comprises the magnetic components of the drive unit 4, which are the posts 40 and the back plate 50, as one single piece or monoblock. The monoblock consists of discontinuous soft magnetic material. The discontinuous soft magnetic material is discontinuous regarding electric conductivity. As shown, it comprises a plurality of sheets 85 of ferromagnetic material which are laminated to each other to form a monoblock 9 as shown in FIG. 11C. The direction of lamination DL is parallel to the axis of rotation 10.

The coil windings 44 extend up to the impeller-side end 420 of the posts 40. This has the advantage that a magnetomotive force can be generated along the complete post 40. The magnetic core 400 comprises a protrusion 401 at the rear end 450 of the posts 40 protruding radially in respect to the posts 40. This protrusion 401 can be a stop for the coil windings 44 towards the back plate 50. As the integral magnetic core 400 has a high rigidity between the back plate 50 and the posts 40, a spacer between the posts 40 at the impeller-side end 420 of the posts may be omitted. The integral magnetic core 400 provides the advantage that an optimum magnetic connection between the posts 40 and the back plate 50 can be achieved. The magnetic core 400 may have a diameter of less than 10 mm.

Figure 11A:
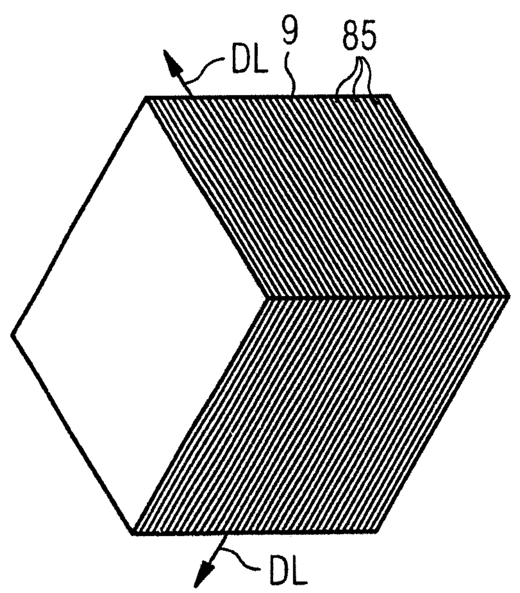
FIGS. 11A to 11C show steps of manufacturing an integrated magnetic core for the drive unit according to FIG. 10.
Figure 11B:
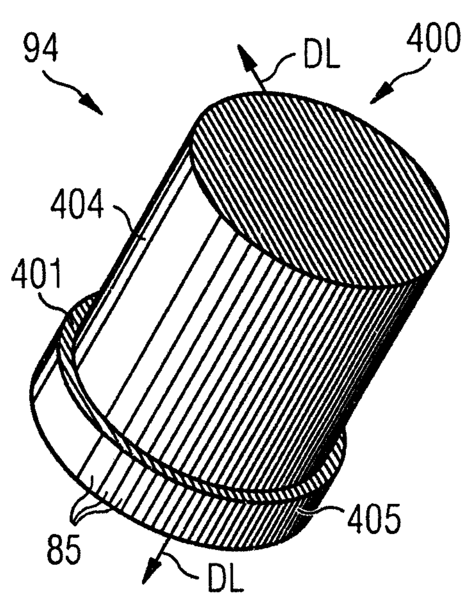
Figure 11C:
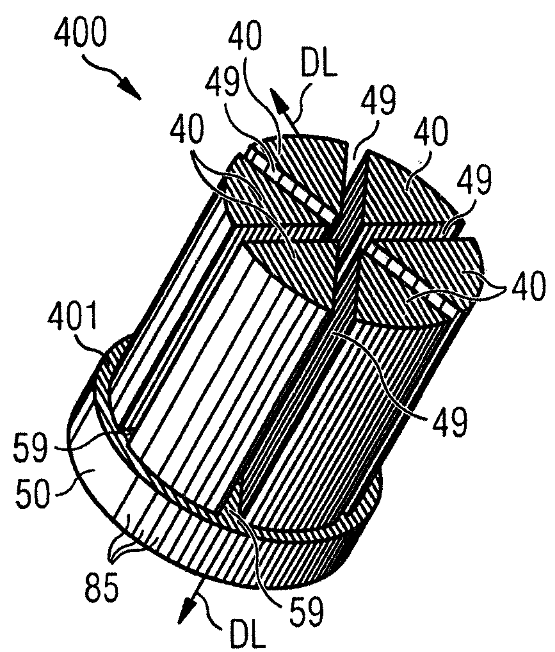

FIGS. 11A to 11C show steps of manufacturing the magnetic core 400 for the drive unit 4 of the drive unit-impeller-arrangement as shown in FIG. 10. FIG. 11A shows in a perspective view a monoblock 9 in cubical shape which forms a work piece for manufacturing the magnetic core 400. The monoblock 9 consists of a discontinuous soft magnetic material which is discontinuous regarding electrical conductivity. It comprises sheets 85 which are oriented in a direction of lamination DL which runs along the main plane of the sheets 85. The sheets 85 are each bonded to their respective neighbouring sheet by a bonding layer of an electrical non-conductive material, which is not explicitly shown in FIGS. 11A to 11C.

FIG. 11B shows the magnetic core 400 in a semi-manufactured state in which it has been machined, e.g. turned, from the cubical monoblock 9 into a substantially cylindrical body 94. In this machining step, the protrusion 401 is manufactured. A section 404 of reduced diameter of the body 94, which forms a peripheral surface of the posts 40 of the magnetic core 400, is manufactured with a diameter that corresponds to an outer radius of the outermost convex side surfaces 842 of the posts 40.

Then, the body 94 can be further manufactured to produce the magnetic core 400 as shown in FIG. 11C. For this production step, electric discharge machining can be used. Especially electric discharge machining by wire cutting can be applied to produce the slots 49 which separate the posts 40 from each other. Inside the slots, space for the coil windings 44 is provided. At the ground of the slots 49, an intermediate area 59 of the integral back plate 50 extends between the rear ends of the posts 40. The intermediate area is integral with the posts 40 and with the back plate 50. Thus, the whole magnetic core is formed by the monoblock 9.

The direction of lamination DL in the magnetic core 400 is such that it is parallel to the axis of rotation 10. It may be tolerated that the direction of lamination DL in the base plate 50 is not parallel with respect to the magnetic flow between the posts 40 in the base plate 50. It is also possible to manufacture the magnetic core 400 from coiled soft magnetic sheet material which is separated by electrically non-conducting layers. Then, the direction of lamination DL in the base plate 50 is always in the circumferential direction which is advantageous to avoid eddy currents in the magnetic flux in the base plate 50.

FIGS. 12A to 12C show how one or more welds may be provided on surfaces of the integrated magnetic core as manufactured according to FIGS. 11A to 11C. Accordingly, in the embodiment shown, three weld seams 82, 83 are provided on one side face of the cubical monoblock 9. The weld seams 82, 83 are welded at a distance to each other and across the cross section of the body 94 to be cut out of the monoblock 9. The weld seams 82, 83 run perpendicular to the direction of lamination DL of the sheets 85. In this way, the sheets of the discontinuous soft magnetic material are connected to each other. Instead of three weld seams, more weld seams or a single wide weld may be provided. In addition, similar weld seams may be provided on the opposite side of the monoblock 9 (not shown). Alternatively or in addition to the welds on the opposite side faces, one or more weld seams may be provided on a side surface of the monoblock 9 at the level of the back plate 50 so as to surround the back plate 50 completely or at least partially. The sheets 85 have a better mechanical connection to each other due to the weld seams 82, 83 and are also electrically connected. The latter has the advantage that electrical current can flow from any position of the discontinuous soft magnetic material to each position of electrical connection of the body 94 which may be required e.g. for electric discharge machining. This way, electrical discharge machining is facilitated significantly. Furthermore, higher process reliability is achieved as the back plate-post unit to be cut-out of the body 94 cannot fall apart by delamination. Preferably, laser welding is applied. It may be advantageous to apply welding power to the same weld twice or even more often.

Figure 13A:
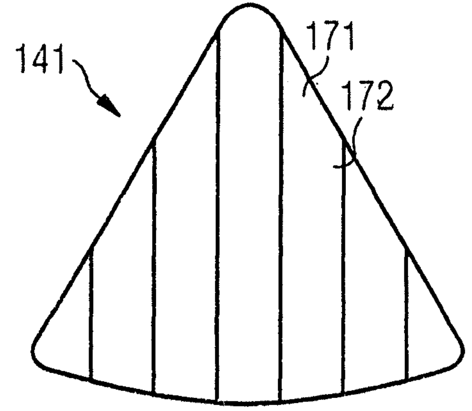
FIGS. 13A to 13J show cross-sections through posts according to various embodiments.
Figure 13B:
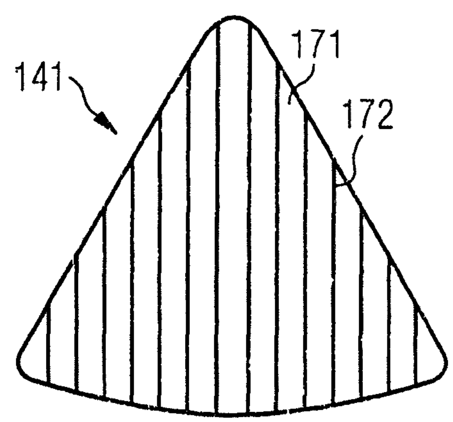
Figure 13C:
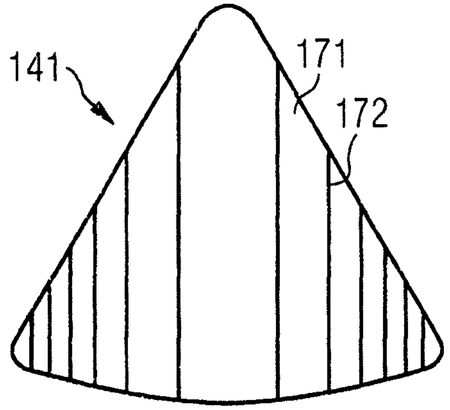
Figure 13D:
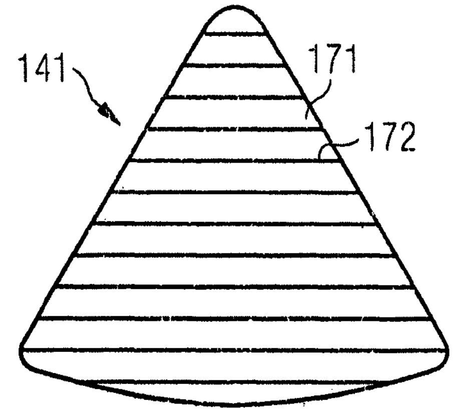

FIGS. 13A to 13J illustrate various embodiments of posts seen in cross section. FIGS. 13A to 13D show embodiments in which the post is slotted, i.e. is formed of a plurality of sheets 171 insulated from each other by insulating layers 172. The insulating layers 172 can comprise adhesive, lacquer, baking enamel or the like. FIGS. 13A and 13B show embodiments in which the thickness of the sheets 171 is uniform. The thickness may be in the range from 25 μm to 450 μm. The sheets 171 shown in FIG. 13A have a greater thickness than the sheets 171 shown in FIG. 13B. The sheets in FIG. 13C have varying thicknesses, with the central sheet having the greatest thickness and the outermost sheets having the smallest thickness. This may be advantageous because eddy currents in the side regions of the posts are more critical and can be reduced by the thin sheets. Eddy currents in the central area are less critical, and the relatively thick central sheet may help in improving the magnetic flux. The orientation of the sheets 171 may be different as exemplarily shown in FIG. 13D as long as the soft magnetic material in the shown cross-section, i.e. the soft magnetic material in cross-section transverse to the direction of the magnetic flux, is discontinuous or interrupted.

Figure 13E:
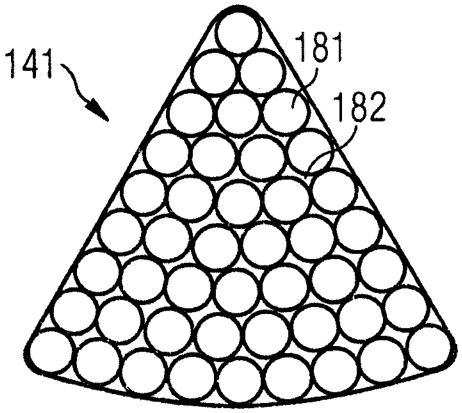
Figure 13F:
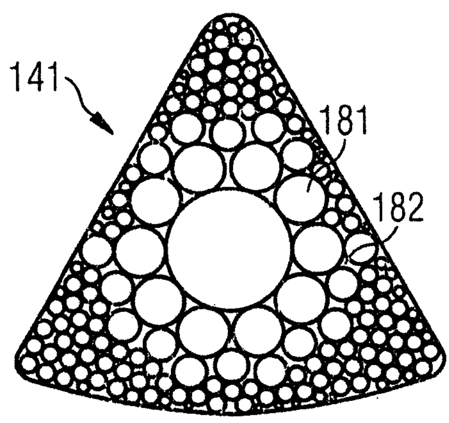
Figure 13G:
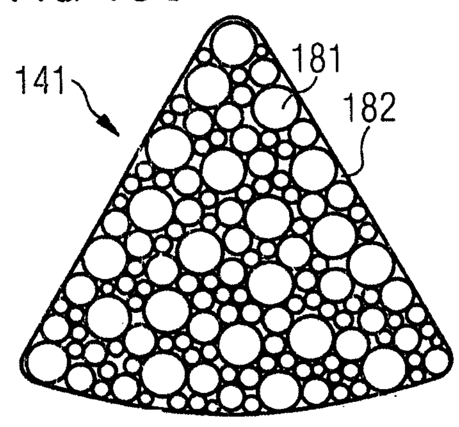
Figure 13H:
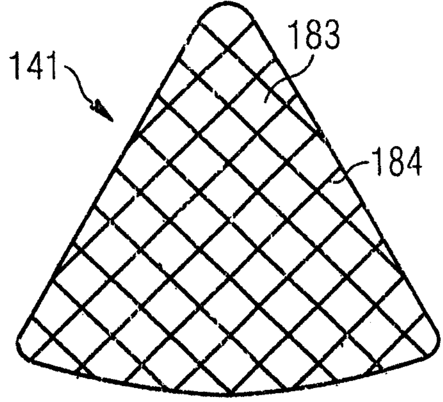
Figure 13I:
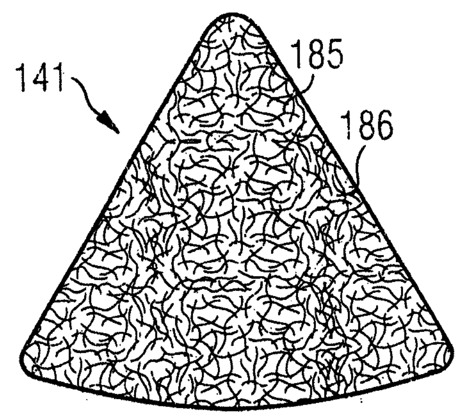

FIGS. 13E and 13F show embodiments in which the posts 141 are formed by a bundle of wires 181 which are insulated from each other by an insulating material 182. The insulating material 182 may be present as a coating of each of the wires 181 or may be a matrix in which the wires 181 are embedded. In the embodiment of FIG. 13E all wires have the same diameter, whereas in the embodiment of FIG. 13F a central wire has a largest diameter and outer wires have smaller diameters, similar to the embodiment shown in FIG. 13C having sheets with varying thicknesses. As shown in FIG. 13G, wires 181 of different diameters may be mixed, which may increase the total cross-sectional area of soft magnetic material compared to embodiments in which all wires have the same diameter. Still alternatively, in order to further minimize insulating layers 184 between the wires 183, the wires 183 may have a polygonal cross-sectional area, such as rectangular, square etc.

Figure 13J:
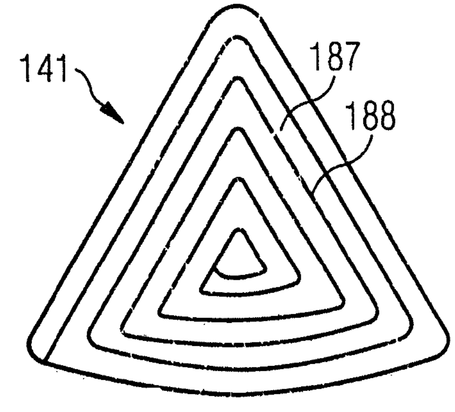

Alternatively, the discontinuous cross-section of the posts 141 may be created by metal particles 185 embedded in a polymer matrix 186 as shown in FIG. 131, or by steel wool or other porous structures impregnated with an insulating matrix. A porous and, thus, discontinuous structure of soft magnetic material may also be produced by a sintering process or high-pressure molding process, in which an insulating matrix may be omitted because insulating layers are formed automatically by oxidation of the soft magnetic material by exposure to air. Still alternatively, the post 141 may be formed of a rolled-up sheet 187 of a soft magnetic material in which the layers of the rolled-up sheet 187 are separated by insulating layers 188 as shown in FIG. 13J. This also provides a discontinuous cross-section in the sense of the present invention which reduces eddy currents in the posts 141 or the posts 40.

The invention claimed is:

1. An intravascular blood pump for percutaneous insertion into a patient's blood vessel, comprising:

a pump casing having a blood flow inlet and a blood flow outlet, an impeller arranged in said pump casing so as to be rotatable about an axis of rotation, the impeller having blades sized and shaped for conveying blood from the blood flow inlet to the blood flow outlet, a drive unit for rotating the impeller, the drive unit comprising a plurality of posts arranged about the axis of rotation and a back plate connecting rear ends of the plurality of posts, wherein the plurality of posts and the back plate form a magnetic core of the drive unit, and a coil winding disposed around each of the plurality of posts, the coil windings being controllable so as to create a rotating magnetic field, wherein the impeller comprises a magnetic structure arranged to interact with the rotating magnetic field so as to cause rotation of the impeller, and wherein at least one post of the plurality of posts comprises a discontinuous soft magnetic material which is discontinuous regarding electric conductivity in a cross-section of the at least one post, wherein at least one weld is provided at a surface of the discontinuous soft magnetic material, the at least one weld bridging at least one discontinuity regarding electric conductivity in the discontinuous soft magnetic material, wherein the discontinuous soft magnetic material comprises a plurality of electrically conducting wires disposed within the at least one post, the plurality of electrically conducting wires insulated from each other by an insulating material.

2. The intravascular blood pump of claim 1, wherein at least one of the at least one weld is arranged at a rear end surface of the at least one post.

3. The intravascular blood pump of claim 1, wherein at least one of the at least one weld is arranged at an impeller-side end surface of the at least one post.

4. The intravascular blood pump of claim 1, wherein at least one of the at least one weld is arranged at an impeller-side end surface of the at least one post and at least one further weld is arranged at a rear end surface of the at least one post.

5. The intravascular blood pump of claim 1, wherein two of the at least one weld are arranged at one end of the at least one post spaced apart from each other.

6. The intravascular blood pump of claim 1, wherein at least one of the at least one weld extends over a side surface of the at least one post.

7. The intravascular blood pump of claim 1, wherein more than one of the at least one weld is arranged on a same surface side of the at least one post.

8. The intravascular blood pump of claim 1, wherein the at least one weld comprises a weld seam bridging the at least one discontinuity regarding electric conductivity in the discontinuous soft magnetic material.

9. The intravascular blood pump of claim 1, wherein the plurality of electrically conducting wires include at least a first wire and a second wire that have different diameters.

10. The intravascular blood pump of claim 1, wherein the plurality of electrically conducting wires each have a circular cross-sectional shape.

11. The intravascular blood pump of claim 1, wherein the plurality of electrically conducting wires each have a polygonal cross-sectional shape.

* * * * *